(12) United States Patent
Shah

(10) Patent No.: US 7,026,454 B1
(45) Date of Patent: Apr. 11, 2006

(54) NEUROENDOCRINE MARKER OF PROSTATE CANCER AND METHOD FOR PRODUCING SAME

(75) Inventor: Girish V. Shah, Amarillo, TX (US)

(73) Assignee: University of Kansas Medical Center, Kansas City, KS (US)

( * ) Notice: Subject to any disclaimer, the term of this patent is extended or adjusted under 35 U.S.C. 154(b) by 0 days.

(21) Appl. No.: 09/251,133

(22) Filed: Feb. 16, 1999

Related U.S. Application Data
(60) Provisional application No. 60/074,809, filed on Feb. 17, 1998.

(51) Int. Cl.
*C07K 16/00* (2006.01)
*C07K 17/00* (2006.01)
*A61K 43/00* (2006.01)
*A61K 39/395* (2006.01)

(52) U.S. Cl. .................... 530/387.1; 530/300; 530/350; 514/2; 424/178.1

(58) Field of Classification Search ................. 530/300, 530/350; 514/2; 424/178.1
See application file for complete search history.

(56) References Cited

U.S. PATENT DOCUMENTS

| | | | |
|---|---|---|---|
| 4,826,813 A | 5/1989 | Huffman et al. | |
| 4,876,243 A | 10/1989 | Marshall et al. | |
| 6,251,613 B1 | 6/2001 | Kishimoto et al. | |

OTHER PUBLICATIONS

Lazar, E. et al. Transforming growth factor alpha: Mutation of aspartic acid 47 and leucine 48 results in different biological activities. Molecular and Cellular Biology, 8(1): 1247–1252, 1988.*
Burgess, W.H. et al. J. Cell Biology, 111: 2129–2138, 1990.*
Accession No. P55062, Database SwissProt, Walter, L. et al. Mamm. Genome 5: 216–221, 1994.*
Accession No. H86387, Database PIR, Mar. 2001.*
Accession No. AAB48241, Database Geneseq, in U.S. Patent 6160202, Dec. 2000.*
Accession No. Q9MS96, Database SPTREMBL, Whitney, S.M. Oct. 2000.*
Lazar, et al., Transforming growth factor alpha: Mutation of aspartic acid 47 and leccine 48 results in different biological activities., Molecular and Cellular Biology, 8 (1), p. 1247–1252, 1988.
Burgess, et al., Possible Dissociation of the heparin–binding and mitogenic activities of heparin–binding (acidic fibroblast) growth facto–1 from its receptor–binding activites by site–directed mutagenesis of a single lysine residue, J. Cell Biology, 111: p. 2129–2138, 1990.
Acession No. P55062, Database SwissProt, Talter, L. et al. Mamm. Genone 5: 216–221, 1994.

Acession No. H86387, Database PIR, Mar. 2001.
Acession No. AAB48241, database Geneseq, In U.S. Patent 6160202, Dec. 2000.
Acession No. Q9MS96, Database SPTREMBL, Whitney, S.M. Oct. 2000.
Cussenot, et al., "Evaluation and clinical valure of neuroendocrine differentiation in human prostatic tumors," The Prostate Supplement, p. 43–51, 1998.
Cohen, et al., "Neuroendocrine differentiation in prostatic adenocarcinoma and its relationship to tumor progression," Cancer, p. 1899–1903, 1994.
Huang et al., "Relation between neuroendocrine expression of prostatic carcinoma an prognosis," Chung. Hua. I. Hsueh. Tsa. Chih, vol. 74, (No. 62), p. 23–25, 1994.
Kadmon et al., "Elevated Plasma chromogranin–a concentrations in prostatic carcinoma," J. Urol., p. 358–361, 1991.
Schumacher et al., "Identification of d–peptide ligands through mirror–image phage display," Science, p. 1854, 1996.
Apostolopoulos, et al., "Muc1 cross–reactive gal alpha (1,2) gal antibodies in humans swithc immune responses from cellular to humoral," Nature Medicine, vol. 4 (No. 3), p. 315–320, 1998.
Samuel, et al., "Immunogenicity and antitumor activity of a liposomal MUC1 peptide–based vaccine," Int. J. Cancer, p. 295–302, 1998.
Foon, et al., "Clinical and Immune responses in advanced colorectal cancer patients treated with anti–idiotype monoclonal antibody vaccine that mimics the carcinoembryonic antigen," Clinical Cancer Research, p. 1267–1276, 1997.
Cole, et al., "Characterization of a sustained–release delivery system for combined cytokine/peptide vaccination using a poly–N–acetyl glucosamine–based polymer matrix," Clinical Cancer Research, p. 867–873, 1997.
Zhang, et al., "Expression of potential targe antigens for immunotherapy on primary and metastatic porstate cancers," Clincal Cancer Research, p. 295–302, 1998.
Kono et al., "Identification of her2/neu–derived peptide epitopes recognized by gastric cancer–specific cytotoxic T lymphocytes," Int. J. Cancer, p. 202–208, 1998.
Prions met Aptamers, www.cyber–dyne.com/–tom/ aptamer.html.
DNA–based vaccine used to fight cancer, www.newswise.com/articels/Cancer.UIC.Html.
Mangoo–Karim, et al., "Renal epithelial cyst formation and enlargement in vitro: dependenc on cAMP," Proc. Natl. Acad.Sci. USA, p. 6007–6011, 1989.

(Continued)

*Primary Examiner*—Anthony C. Caputa
*Assistant Examiner*—Christopher Yaen
(74) *Attorney, Agent, or Firm*—Joseph A. Mahoney; Christine M. Rebman; Mayer, Brown, Rowe & Maw LLP

(57) ABSTRACT

The present invention involves a novel neuroendocrine growth factor or marker ("NEM") identified in cultured prostate cancer cells and conjugates of NEM and a binding agent capable of inhibiting binding of NEM to its receptor.

14 Claims, 12 Drawing Sheets

OTHER PUBLICATIONS

Cowley, et al., "Elevated c–myc protooncogene expression in autosomal recessive polycystic kidney disease," Pro. Natl. Acad. Sci. USA, p. 8394–98, 1987.

Grantham et al., "Cyst formation and frowth in autosomal dominatn polycystic kidney disease", Kidney Int., p. 1145–1152, 1987.

Carone et al., "Basement membrane antigens in renal polycystic disease," Am. J. Pathol., p. 466–471, 1988.

Grantham et al., "Chemical modification of cell proliferation and fluid secretion in renal cysts," Kidney Int., p. 1379–1389, 1989.

Davidow et al., "The cystic fibrosis transmemebrane conductance regulatro mediates transepithelial fluid secretion by human autosomal dominant polycystic kidney disease epithlium in vitro," Kidney Int., vol. 50 (No. 1), p. 208–218, 1996.

Yamaguchi et al., "Renal accumulation and excretion of cyclic adenosine monophosphate in a murine model of slowly porgressive polycystic kidney disease," Am. J. Kidney Dis., vol. 30 (No. 5), p. 703–709, 1997.

Carmichal et al., "Molecular biology of vasopressin receptors," Sem. in Nephrology, vol. 14 (No. 4), p. 341–348, 1994.

Fushimi, Sasaki, et al., "Cloning and expression of apical membrane water channel of rat kidney collecting tubule," Nature, p. 549–552, 1993.

Yamamura et al., "Characterization of a Novel Aquaretic agen, OPC–31260, as an orall effective, nonpeptide vasopressin V2 receptor antagonist," British J. Pharm., p. 787–791, 1992.

Laszlo, et al., "Pharmacology and clinical Perspectives of Vasopressin Antagonists", Pharmacol. Rev., p. 73–108, 1991.

Mah, et al., "Antagonists of arginine–casopressin: experimental and clinical applications," Drugs Future, p. 1055–1070, 1987.

Manning et al., "Discovery, development, and some uses of vasopresin and oxytocin antagonists," J. Lab. Clin. Med., p. 617–632, 1989.

Sorensen, et al., "Syndrome of inappropriate secretion of antidiuretic hormone (SIADH) in malignant disease," J. Int. Med., p. 97–110, 1995.

Serradeil–Le Gal, et al., "Characterization of SR121463A, a highly potent and selective, orally active vasopressin 2 receptor antagonist," J. Clin. Invest., vol. 98 (No. 12), p. 2729–2738, 1992.

Shimiau K., "Aquaretic effects of the nonpeptide V2 antagonist OPC–31260 in hydrpenic humans," Kidney International, p. 220–226, 1995.

Ning, et al., "Forskolin stimulates camp production by stimulating vasopressin V2 receptors," J. Am. Soc. Neph, p. 23, 1997.

Schwartz et al., J. Clin. Invest. 90, 1275, 1992.

Di Sant'Agnesse et al.,, "Neuroendocrine differentiation in prostatic malignancy," Cancer, ed., vol. 78 (No. 2), p. 357–361, 1996.

Zhau et al.,, "Biomarkers associated with prostate cancer porgression," Journal of Cellular Biochemistry, Supplement, p. 208–216, 1994.

Hoosein, N.M., "Neuroendocrine and immune mediators in prostate cancer progression," Frontiers in Biosciene, p. D1274–1285, 1998.

* cited by examiner

PIN 1

MODERATE GRADE 1

HIGH GRADE 1

BPH 1

PIN 2

LOW GRADE 1

MODERATE GRADE 2

HIGH GRADE 2

VERY AGGRESSIVE 1

LIVER METASTASIS

LYMPH NODE METASTASIS

TONSILS (NEGATIVE CONTROL)

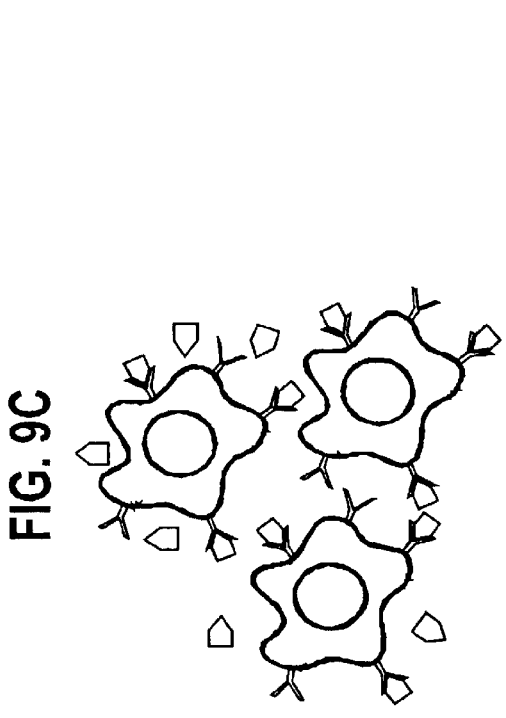
FIG. 9C
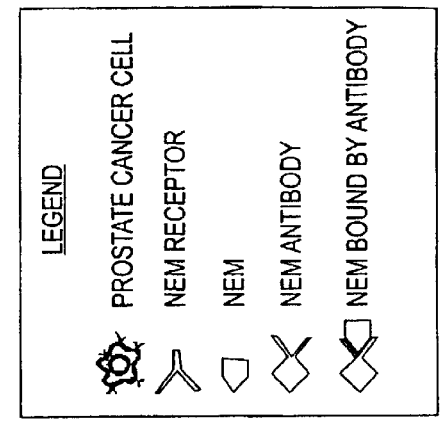
FIG. 9B
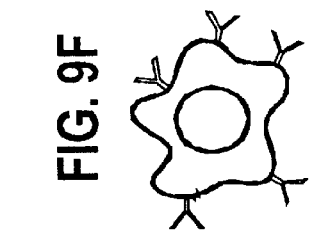
FIG. 9F
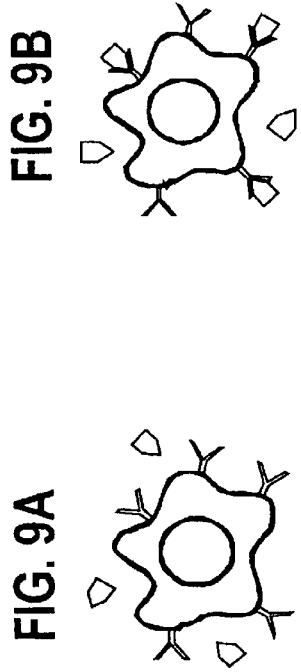
FIG. 9A
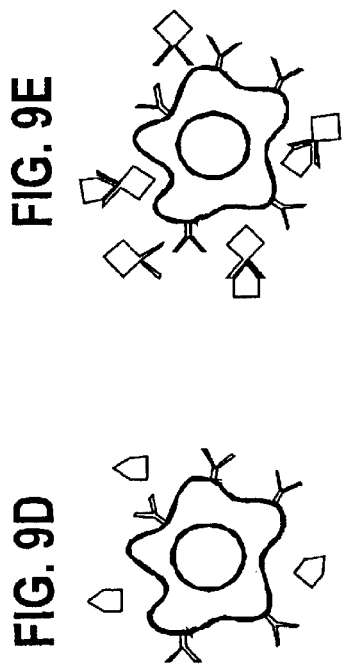

LEGEND
PROSTATE CANCER CELL
NORMAL CELL
NEM-RADIOISOTOPE CONJUGATE
NEM RECEPTOR

SEQUENCE LISTING

```
<160> NUMBER OF SEQ ID NOS:   12

<210> SEQ ID NO 1
<211> LENGTH: 48
<212> TYPE: PRT
<213> ORGANISM: Homo sapiens

<400> SEQUENCE: 1

Cys Ser Val Lys Ser Thr Ser Cys Val Ser Lys Val Lys Phe His Phe
1               5                   10                  15

Asn His Met Gln Asp Ile Pro Gln Arg Tyr Arg Gln Val Asp Cys Ile
            20                  25                  30

Phe Phe Leu Phe Ser Phe Ser Phe Phe Ser Glu Leu Gly Thr Glu Pro
        35                  40                  45

<210> SEQ ID NO 2
<211> LENGTH: 691
<212> TYPE: DNA
<213> ORGANISM: Homo sapiens
<220> FEATURE:
<221> NAME/KEY: Unsure
<222> LOCATION: (200)..(686)
<223> OTHER INFORMATION: N is unknown

<400> SEQUENCE: 2
agaacctgtg tgctgggcta cctgcatata gtgctcagta ctgagtacta gctgtgtttc      60
cttagtcctg tttcacttta accatatgca agacattcct caacgttata ggcaagtaga    120
ctgcatcttt tttctttttt cttttctttt tttctcggag ctggggaccg aacccaggac    180
cttgcgcttg ctaggccasn cntnaccact gagctaaatc cccaaccccg actgcatcgt    240
ttttggtttt tagttaaatt ccggtttgct ctatttcgtg ttccctttgt ttaaaagaaa    300
ctgtagccgg ggtagtatat gtctataatc ccagcagttg ggaggcagga ggatccagag    360
ttcaagtcgg catggaacac atgagacatt agctcaaaaa aaaaaaaaaa aaaagtcgac    420
tgagaattcc acaatcccgc ggccatggcg gcsgggagca tgcgacgtcg ggcccaattc    480
gccctatagt gagtcgtatt acaattcact ggccgtcgtt tttacaacgt cgtgactggg    540
aaaaccctgg cgttacccaa cttaatcgct tgcagcacat ccccttttcgc agctggctaa    600 tagcgagagg cccgcaccga tcgccctccc aacagttgcg caccggaatn gcgaatggac    660
gcgccctgta gcgncattaa gggcgngtgt c                                    691

<210> SEQ ID NO 3
<211> LENGTH: 433
<212> TYPE: DNA
<213> ORGANISM: Homo sapiens
```

```
<400> SEQUENCE: 3
agaacctgtg tgctgggcta cctgcatata gtgccagagt tcatcgaatc tcagctgctg      60
gggctcctta gtcctgtttc actttaacca tatgcaagac attcctcaac gttataggca     120
agtagactgc atctttttt ttcttttttt ttctttttct tttttctttt tttcggagct      180
ggggaccgaa cccaggacct tgcgcttgct aggcaagcgc tctaccactg agctaaatcc     240
ccaaccccga ctgcatcgtt tttggttttt agttaaattc cggtttgctc tatttcgtgt     300 tcctttgtt taaaagaaac tgtagccggg gtagtatatg tctataatcc cagcagttgg      360
gaggcaggag gatccagagt tcaagtcggc atggcacaca tgagacatta gctcaaaaaa     420
aaaaaaaaaa aaa                                                        433

<210> SEQ ID NO 4
<211> LENGTH: 432
<212> TYPE: DNA
<213> ORGANISM: Homo sapiens

<400> SEQUENCE: 4
agaacctgtg tgctgggcta cctgcatata gtgccagagt tcatcgaatc tcagctgctg      60
gggctcctta gtcctgtttc ctttaaccat atgcaagaca ttcctcaacg ttataggcaa     120
gtagactgca tctttttttt tctttttttt tcttttttctt ttttcttttt ttcggagctg    180 ggaccgaac ccaggacctt gcgcttgcta ggcaagcgct ctaccactga gctaaatccc      240
caaccccgac tgcatcgttt ttggtttta gttaaattcc ggtttgctct atttcgtgtt     300
ccctttgttt aaaagaaact gtagccgggg tagtatatgt ctataatccc agcagttggg    360
aggcaggagg atccagagtt caagtcggca tggcacacat gagacattag ctcaaaaaaa    420
aaaaaaaaaa aa                                                         432

<210> SEQ ID NO 5
<211> LENGTH: 435
<212> TYPE: DNA
<213> ORGANISM: Homo sapiens

<400> SEQUENCE: 5
attagaacct gtgtgctggg ctacctgcat atagtgccag agttcatcga atctcagctg      60
ctggggctcc ttagtcctgt ttcctttaac catatgcaag acattcctca cgttatagg      120 caagtagact gcatcttttt ttttcttttt ttttctttt ctttttttctt ttttcggag      180 ctggggaccg aacccaggac cttgcgcttg ctaggcaagc gctctaccac tgagctaaat    240
ccccaacccc gactgcatcg ttttggttt ttagttaaat tccggtttgc tctatttcgt     300
gttccctttg tttaaaagaa actgtagccg ggtagtata tgtctataat cccagcagtt     360 ggggaggcagg aggatccaga gttcaagtcg gcatggcaca catgagacat tagctcaaaa    420
aaaaaaaaaa aaaaa                                                      435

<210> SEQ ID NO 6
<211> LENGTH: 28
<212> TYPE: PRT
<213> ORGANISM: Homo sapiens

<400> SEQUENCE: 6

Arg Thr Cys Val Leu Gly Tyr Leu His Ile Val Pro Glu Phe Ile Glu
1               5                   10                  15

Ser Gln Leu Leu Gly Leu Leu Ser Pro Val Ser Leu
            20                  25
```

```
<210> SEQ ID NO 7
<211> LENGTH: 9
<212> TYPE: PRT
<213> ORGANISM: Homo sapiens

<400> SEQUENCE: 7

Glu Pro Val Cys Trp Ala Thr Cys Ile
1               5

<210> SEQ ID NO 8
<211> LENGTH: 22
<212> TYPE: PRT
<213> ORGANISM: Homo sapiens

<400> SEQUENCE: 8

Asn Leu Cys Ala Gly Leu Pro Ala Tyr Ser Ala Arg Val His Arg Ile
1               5                   10                  15

Ser Ala Ala Gly Ala Pro
            20

<210> SEQ ID NO 9
<211> LENGTH: 103
<212> TYPE: PRT
<213> ORGANISM: Homo sapiens

<400> SEQUENCE: 9

Arg Thr Cys Val Leu Gly Tyr Leu His Ile Val Pro Glu Phe Ile Glu
1               5                   10                  15

Ser Gln Leu Leu Gly Leu Leu Ser Pro Val Ser Phe Asn His Met Gln
            20                  25                  30

Asp Ile Pro Gln Arg Tyr Arg Gln Val Asp Cys Ile Phe Phe Phe Leu
        35                  40                  45

Phe Phe Ser Phe Ser Phe Phe Phe Ser Glu Leu Gly Thr Glu Pro
    50                  55                  60

Arg Thr Leu Arg Leu Leu Gly Lys Arg Ser Thr Thr Glu Leu Asn Pro
65                  70                  75                  80

Gln Pro Arg Leu His Arg Phe Trp Phe Leu Val Lys Phe Arg Phe Ala
                85                  90                  95

Leu Phe Arg Val Pro Phe Val
            100

<210> SEQ ID NO 10
<211> LENGTH: 9
<212> TYPE: PRT
<213> ORGANISM: Homo sapiens

<400> SEQUENCE: 10

Glu Pro Val Cys Trp Ala Thr Cys Ile
1               5

<210> SEQ ID NO 11
<211> LENGTH: 22
<212> TYPE: PRT
<213> ORGANISM: Homo sapiens

<400> SEQUENCE: 11

Asn Leu Cys Ala Gly Leu Pro Ala Tyr Ser Ala Arg Val His Arg Ile
1               5                   10                  15

Ser Ala Ala Gly Ala Pro
            20
```

-continued

```
<210> SEQ ID NO 12
<211> LENGTH: 29
<212> TYPE: PRT
<213> ORGANISM: Homo sapiens

<400> SEQUENCE: 12

Ile Arg Thr Cys Val Leu Gly Tyr Leu His Ile Val Pro Glu Phe Ile
1               5                   10                  15

Glu Ser Gln Leu Leu Gly Leu Leu Ser Pro Val Ser Leu
            20                  25
```

NEUROENDOCRINE MARKER OF PROSTATE CANCER AND METHOD FOR PRODUCING SAME

RELATED APPLICATION

This application is based on U.S. Provisional Application Ser. No. 60/074,809 filed Feb. 17, 1998.

FIELD OF THE INVENTION

The present invention relates generally to markers for cancer diagnosis and treatment, and more specifically, to a novel neuroendocrine growth factor to diagnose and treat invasive and metastatic prostate cancer and other cancers that express this growth factor.

BACKGROUND

Prostatic carcinoma is the leading malignancy in human males in terms of incidence and the second leading cause of cancer deaths in men. While a majority of prostatic carcinomas remain dormant for a long period of time, a significant minority of them displays rapid growth and invasive characteristics. The mechanisms responsible for the latent growth of tumors in a majority of cases and for rapid progression in a minority of cases have not been identified. It has been suggested that tumors with greater neuroendocrine cell populations may display autonomous growth, androgen-independence and increased invasiveness. See Cohen et al., *Neuroendocrine Differentiation in Prostatic Adenocarcinoma and Its Relationship to Tumor Progression,* CANCER 74:1899–1903 (1994); Huang et al., *Relation Between Neuroendocrine Expression of Prostatic Carcinoma and Prognosis,* CHUNG. HUA. I. HSUEH. TSA. CHIH. 74:23–5, 62 (1994); Kadmon et al., *Elevated Plasma Chromogranin-A Concentrations in Prostatic Carcinoma,* J. UROL. 146:358–61 (1991).

The major therapeutic approach for the treatment of prostate cancer is androgen-deprivation through chemical means or surgical removal of the tumor. Indeed, patients with advanced prostatic carcinoma (PC) as well as experimental in vitro PC models respond largely to various methods of androgen deprivation such as orchiectomy, administration of estrogens, anti-androgens and analogs of gonadotropin-releasing hormone (LH-RH). However, a significant population of these individuals also exhibits tumor relapse in 18–36 months. Relapse and the subsequent spread of prostate cancer cells have been associated with androgen-insensitivity. Therefore, a possible cause of relapse, local invasion, and metastasis is the proliferation of androgen-insensitive clones. That is, those cancer cells which require androgens for growth die when they are deprived of androgens during therapy, but those aggressive androgen-independent prostatic carcinoma cells ("AIPC cells") continue to proliferate even in the absence of androgens. Two areas of prostate cancer biology currently under intense investigation include: (1) the cause of relapse of prostate carcinoma in patients who initially respond to androgen deprivation treatments; and (2) the early detection of prostatic carcinomas that will become metastatic. Once the relapse occurs, few treatment options are available and eventually the patient dies from the disease. Continued proliferation of clonally derived AIPC tumor cells is believed to be the underlying cause of the relapse, as metastatic tumors are frequently found to be androgen-independent. Although AIPC cells are by definition independent from influence by androgens, there are neuroendocrine and other growth factors, which can stimulate their growth. Tumor cells are known to express distinct markers at the very early stage of transformation. Several tumor markers have been identified and have been used to identify either the presence of malignancy and/or the severity of the malignancy. For example, prostate-specific antigen (PSA) has been identified and used for the diagnosis of prostate cancer. Although PSA has been used as a marker for PC for several years, current evidence suggests that serum PSA levels: (1) do not always correlate with progression of the disease; (2) are not expressed in a small but significant number of aggressive PCs which therefore are undetected by PSA screening; and (3) do not predict the clinical nature of the tumor, i.e., even if the tumor is detected early, PSA screening does not predict whether the tumor will be dormant and therefore relatively harmless, or will be aggressive requiring immediate clinical intervention. Although PSA is used as a diagnostic marker for PC, neither PSA nor other serum markers can reliably identify the metastatic phenotype. Given the fact that not all prostate tumors secrete or express PSA, there is a critical need to develop other markers to identify metastatic phenotypes and PSA negative PC subtypes.

Substantial evidence exists suggesting the role of neuroendocrine growth factors in regulation of AIPC cells. For example, neuroendocrine factors such as bombesin and vasoactive intestinal polypeptide have been shown to influence the invasive behavior of prostate cancer cell lines. Other factors not necessarily regarded as exclusively neuroendocrine in origin, but secreted by neuroendocrine cells such as epidermal growth factor and somatostatin, have also been shown to influence either the invasive characteristics or growth of prostate cancer cell lines. Pindobind, a serotonin Hla receptor antagonist, has been shown to inhibit the growth of prostate cancer cell lines. In addition, foci of neuroendocrine differentiation have been demonstrated in between 47% and 100% of prostate cancers using a combination of sensitive argyrophil staining and immunocytochemistry. Thus, it is likely that neuroendocrine factors play an important role in prostate cancer.

Grade of the cancer determines the severity of the cancer and varies from low to high grades. Low grade prostate tumor grows very slowly and often does not require any aggressive forms of therapy. However, high-grade prostate tumor grows and metastasizes aggressively and requires aggressive therapeutic intervention. Determination of the grade of prostate tumor is crucial for the choosing the right form of therapy. Present methods of determination of the grade of prostate cancer involve examination of the architecture of the prostate tumor in sections of biopsy. However, this method is prone to error due to the fact that there is considerable inter-observer variation leading to wrong diagnosis of the grade of the tumor. Determination of the grade of the tumor based on a biochemical marker rather than the visual observation of the architecture of the tissue would provide a better method for identifying the grade of the tumor. This has led to major efforts at identifying new biochemical markers for prostate cancer.

The present invention involves a novel neuroendocrine growth factor or marker ("NEM") identified in cultured prostate cancer cells. A significantly higher number of binding sites for this novel NEM is present on membranes of prostatic cancer cells than on those of benign prostatic hypertrophy (BPH), a common benign enlargement of the prostate in older men. The ability to differentiate BPH from malignancy is highly important but cannot be effectively accomplished using PSA screening, the most commonly used method for detecting the presence of prostate cancer clinically. The limitations of PSA screening are overcome by screening patient blood for NEM which will identify metastatic prostate cancer, distinguish it from BPH, and can be used in excised tissues to identify the type of cancer and grade its degree of malignancy. Lastly, inhibition of NEM in turn decreases prostatic cancer growth, invasion and metastasis. As such, NEM antagonism offers new modes of therapy for prostate cancer. The data also shows that the expression of NEM in prostate cancer tissues increases with the grade of the cancer. While there is very little or no NEM expression of NEM in BPH (a non-cancerous condition) NEM expression can be seen in all prostate cancer tissues starting as early as the PIN stage, which is considered to be a precursor of invasive cancer. Hence the data shows that NEM is a good biochemical marker for prostate cancer.

SUMMARY OF THE INVENTION

The invention describes a novel growth factor or marker (NEM) isolated from prostate cancer cells that induces the growth and invasion of prostate cancer cells and other cancer cells, and is closely associated with the grade of prostate cancer. One mechanism by which NEM induces the growth of cancer cells is by binding to its receptor (NEM receptor) present on cancer cells which then induces growth and invasion. Blocking the interaction of NEM with its receptor by using an antibody directed against NEM or its receptor would inhibit the growth and invasion of these cancer cells thereby providing therapeutic benefits.

NEM is prepared by first subcloning the complementary DNA in a vector. The plasmid containing NEM cDNA is then transfected in prostate cancer cell line PC-3M cells, and after incubation and culturing, the expressed protein is obtained by affinity chromatography. Standard automated chemical synthesis and purification can also make the protein.

Polyclonal antibodies to NEM are prepared by injecting rabbits with antigen and removing a blood sample after the immune response has occurred. The immunoglobulin fraction of the serum is purified and used as the antiserum. More specific monoclonal antibodies are also prepared which can recognize a single antigenic determinant.

The inventive polyclonal and monoclonal antibodies and the novel probes are utilized in the detection of NEM in tissues and body fluids and grading of invasive and metastatic prostatic cancers and other cancers that exhibit enhanced production of NEM as well as those cancers which are PSA negative. This is successfully accomplished using immunohistochemistry, radioimmunoassay, enzyme-linked immunosorbent assay (ELISA), sandwich ELISA, EIA, fluoroimmunoassay, and chemiluminescence assay techniques, or other techniques used for the detection of peptides.

To create probes to detect complementary NEM mRNA in tissues by in-situ hybridization, cDNA for NEM is cloned into pGEM-T plasmids (Promega) and linearized with Sac II to make antisense strands and with PstI to make sense strand. The transcription reaction and digoxigenin 11-UTP (Boehringer Mannheim, Indianapolis, Ind.) labeling are performed with either SP6 (antisense) or T7 (sense) RNA polymerase provided in the riboprobe labeling kit (Promega). The labeled probes are digested with deoxyribonuclease (Boehringer), extracted with pheno-chloroform, and purified with TE Microselect-D G-50 spin columns (5 Prime-3Prime, Inc., Boulder, Colo.). The inventive antisense RNA (or nucleotide) probes against NEM can be used for detecting the presence of NEM RNA in prostatic and other cancer tissues that express NEM in order to determine the grade of the cancer. Primers based on the DNA sequence can also be used to determine the presence of disseminated prostatic and other cancer cells producing NEM to monitor the presence of metastasis.

The inventive NEM (or NEM receptor) antiserum and monoclonal antibodies inhibit the invasiveness of the disease and, thus, offer new forms of cancer therapy. For example, the polyclonal and monoclonal antibodies of the present invention are conjugated to chemotherapeutic agents and/or radionuclides to treat prostate cancer or other cancers that produce NEM or whose growth is enhanced by NEM. Gene therapy techniques and the preparation of an antagonist to prostatic NEM (or its receptor) can also be employed to treat the disease.

It is therefore a primary object of the present invention to provide a method for preparing NEM and NEM receptor from tissue-cultured prostatic carcinoma cells and from prostatic tissues and by chemical methods of synthesis and purification through the use of recombinant DNA methods.

It is another object of the present invention to provide a method for preparing the corresponding oligonucleotides, which are used as probes to detect NEM in MRNA in tissues by in-situ hybridization.

It is a further object of the present invention to provide a method for identifying unknown metastases and for the grading of prostatic carcinomas.

It is yet another object of the present invention to provide a method for detecting metastatic prostatic cancer as well as PSA-negative prostatic cancers by measuring NEM immunoreactivity in tissues and in human fluids.

It is a still further object of the present invention to provide a method for making NEM antibodies, which are then therapeutically administered to inhibit the growth invasion of prostatic carcinoma and other cancers whose growth is influenced by NEM.

It is yet another object of the present invention to use NEM and antibodies against NEM to the target radionuclides for detecting the presence of primary and secondary sites of prostate cancer.

Yet another object of the present invention is to use NEM, antibodies against NEM or NEM receptor to target cell-killing radionuclides or other cytotoxic agents to cancer cells that selectively bind NEM to preferentially kill these cells.

Another object of the present invention is to use NEM as a prophylactic or therapeutic vaccine whereby these molecules in conjunction with other immunostimulatory molecules stimulate an immune response against cancer cells expressing these molecules to kill these cells. Alternatively, NEM antibodies generated in the body by these procedures will neutralize NEM thereby providing therapeutic benefit.

It is yet another object to use peptides (D or L form) or other small molecules that bind NEM in order to neutralize its growth and invasion-inducing action.

Further, another objective is to use antisense molecules, ribozymes and triplex molecules targeted against NEM to interfere with the synthesis of NEM to produce therapeutic benefits for cancer.

These and other objects, features and advantages of the present invention are more readily understood by those of ordinary skill in the art from the following more detailed description of the preferred embodiments taken with reference to the accompanying figures.

BRIEF DESCRIPTION OF THE DRAWINGS

FIG. 5 is a series of immunohistochemistry photographs of prostatic cancer tissue samples using antibodies to prostatic NEM, and illustrating the degree of malignancy correlating with an amount of NEM expression.

FIG. 9 is a schematic illustrating the mechanism of action pathway of an NEM-based cancer therapy as compared to an untreated cancer pathway.

DETAILED DESCRIPTION OF THE PREFERRED EMBODIMENT

As illustrated in FIGS. 9 and 10, a mechanism of the proliferation and invasion of prostate cancer cells identified by Applicant relates to NEM's stimulation of a receptor on prostate cancer cells.

1. Preparation of Prostatic NEM

Amino acid SEQ ID NO: 6 was prepared by first subcloning the complementary DNA SEQ ID NO: 3 in pRC vector (Invitrogen, San Diego, Calif.). The vector contains cytomegalovirus promoter upstream of the cloning site, and ensures high level expression of the cloned cDNA. The pRC plasmid containing NEM cDNA is then transfected in prostate cancer cell line PC-3M cells using Lipofectamine (Life Technologies, Inc., Gaithersburg, Md.). In brief, PC-3M cells were plated at a density of 15,000 cells per well in a six-well culture plate and transfected 24 hours later with either the vehicle plasmid or the plasmids carrying cDNAs. Aliquots containing 2 mg plasmid and 4 mg Lipofectamine in 1 ml serum-free, protein-free Dulbecco's Modified Eagle's medium (DMEM) were incubated for 45 minutes and added to culture wells. The transfection media was replaced with the complete medium 16 hours later. Two days later, the cells were cultured in selection medium (complete medium containing 400 mg/ml of G418). Individual colonies of the transfectants (NEM PC-3M) were selected after four weeks of culture, dispersed with trypsin/EDTA and propagated further into fresh flasks. The conditioned media was collected, the cells are lysed with a cocktail of detergents and the expressed protein in both these fractions was obtained by affinity chromatography using ProBond™ resin (as described by manufacturer's protocol, Invitrogen).

NEM isolated by Applicant and the purified DNA are being deposited with the American Type Culture Collection, 10801 University Blvd., Manassas, Va. 20110.

SEQ ID NOs: 2–5 are alternative cDNA sequences derived from the isolated NEM cDNA based on Applicant's research and within reasonable margins for error. Peptide SEQ ID NOs: 1, 6–8, 9–11, 12 are alternative sequences based on the cDNA Sequence IDs depending on the reading frame employed to translate same.

2. Dose-Dependent Relationship of NEM on DNA Synthesis in PC-3M Cell Line

Figure 1:
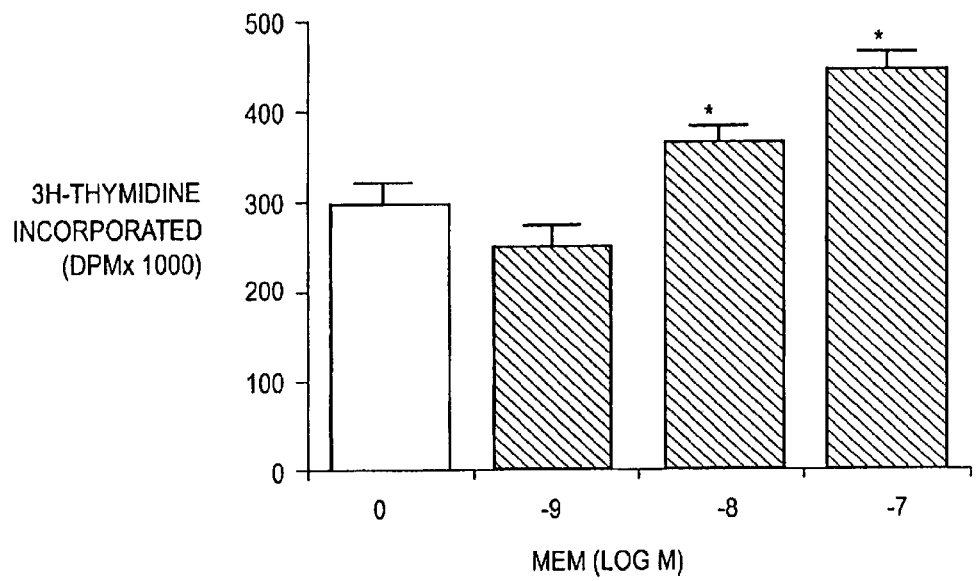
FIG. 1 is a bar graph illustrating the effect of exogenously added prostatic NEM on DNA synthesis of an aggressive prostate cancer cell line, PC-3M.

FIG. 1 illustrates the effect of exogenously added prostatic NEM on DNA synthesis of an aggressive prostate cancer (PC-3M) cell line. To obtain the results shown in FIG. 1, PC-3M cells were seeded at a density of 10,000 cells per well and incubated overnight in the complete medium. The cells were then washed with and incubated in serum-free medium containing the agents and 0.5 µCi of 3H-thymidine for 24 hours. At the end of incubation, the cells were washed three times with PBS-1 µM thymidine and the incorporated radioactivity was determined in TCA-precipitable fraction. The results suggest that NEM stimulated 3H-thymidine incorporation in a dose-dependent fashion, and the increase in DNA synthesis produced by 10 nM or greater concentrations of NEM was significant. NEM also stimulates the growth of certain non-prostate cancer cells like certain bone-derived cell lines (OVCA-5), thereby extending the use of NEM in other cancers that produce or are stimulated by NEM.

3. Preparation of Anti-NEM Serum

Two rabbits weighing about 2 kg each were immunized by 240 µg NEM(1–24)-KLH conjugate (NEM conjugated to keyhold limpet hemocyanin according to published procedures) in complete Freund's adjuvant. Booster doses of 120 µg NEM(1–24)-KLH in incomplete Freund's adjuvant were given every 10 days after the primary injection. The rabbits were bled 10 days after the third booster dose, and antibody production was monitored using an enzyme-amplified enzyme-linked immunosorbent assay technique with NEM as the antigen on the solid phase. In this procedure, the cell lysate (50 µl) from NEM-PC-3M cells was coated on ELISA plates. This served as the solid antigen phase. The anti-NEM rabbit serum was added to the wells at various concentrations (dilutions of 10–100) as the solid antigen phase. The serum was then washed off with phosphate buffered saline and the solid phase was incubated with biotinylated Anti-rabbit gamma globulin. After incubation for 2 hours at room temperatures, the plates were washed and incubated with streptavidin-alkaline phosphatase (Sigma Chemical Co., St. Louis, Mo.). After thorough washing of the solid phase three times, the color reaction was initiated using BCIP-NBT substrate system (Bio-Rad, CA) according to the manufacturer's protocol.

4. Stimulation of Invasiveness of PC-3M Cells by NEM

Figure 2:
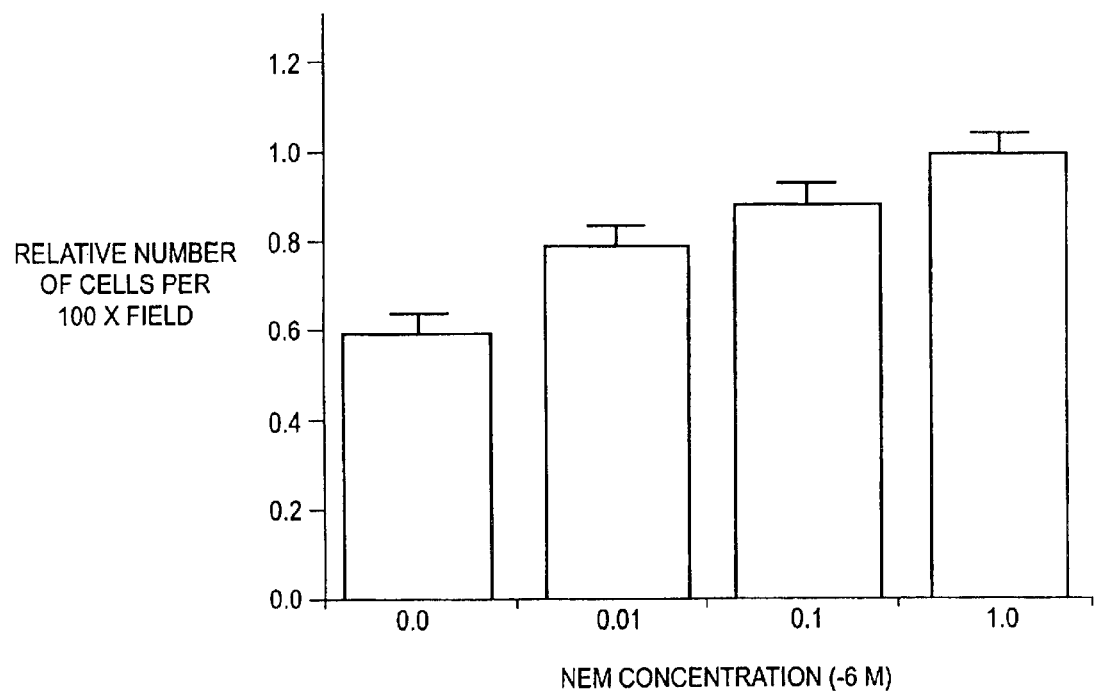
FIG. 2 is a bar graph illustrating a dose-dependent relationship between the concentration of prostatic NEM and the invasiveness of PC-3M cells.

FIG. 2 illustrates the effect of NEM on in vitro invasion of PC-3M cells. The experiment used 3 well Matrigel invasion chambers (Becton Dickinson, Bedford, Mass.). Approximately 200,000 PC-3M cells were seeded in the upper chamber in RPMI 1640 medium containing 0.1% BSA (Sigma, St. Louis), 4 mM L-glutamine, 100 IU/ml penicillin G and 100 ug/ml streptomycin. The lower chamber medium contained chemoattractant medium consisting of 80% complete medium (RPMI 1640, 12% horse serum, 4% heat activated fetal calf serum, 4 mM L-glutamine, 100 IU/ml penicillin G and 100 mg/ml streptomycin). Different concentrations of NEM or conditioned media from NEM-PC3-M cells that express NEM (dilutions ranging from 1 to 5) were added to the upper chamber. The experiments were carried out for 72 hours. At the end of the incubation period the Matrigel was scraped off using cotton swabs and the top insert was fixed and stained using Diff Quick staining (Dade Diagnostics, Aguada, PR). The relative invasive potential was determined by normalizing for cell growth. This was done by plating 100,000 cells in six well dishes in chemoattractant medium and determining the relative growth of cells after 72 hours. The number of cells per 100×field were expressed as mean +/−SEM.

FIG. 2 demonstrates that NEM in a dose-dependent fashion significantly increases the invasiveness of PC-3M cells. The cells demonstrated a 70% increase from 0M to $10^{-6}$M NEM. All concentrations of NEM were significant in comparison to 0 CT for PC-3M. (P<0.05).

5. Inhibition of Growth of PC-3M Cells with Anti-NEM Serum

Figure 3:
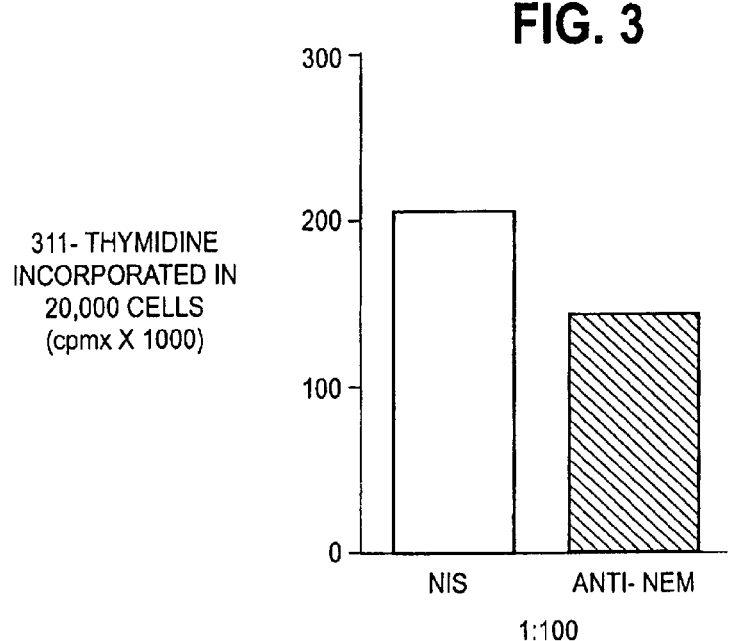
FIG. 3 is a bar graph illustrating a dose-dependent inhibition of growth of PC-3M cells by antibodies to prostatic NEM (dilution of 1:100).

If NEM-induced DNA synthesis may influence proliferative activity of a prostate tumor and other cancer cells, then its immunoneutralization should reduce the growth. This hypothesis was tested by studying the rate of 3H-thymidine incorporation in PC-3M prostate cancer cells. The cells were treated either with non-immune antiserum or anti-NEM antiserum at a final dilution of 1:50. The results presented in FIG. 3 show that anti-NEM antiserum significantly inhibited DNA synthesis in PC-3M cells.

6. Inhibition of Invasion of PC-3M Cells with Anti-NEM Serum

Figure 4:
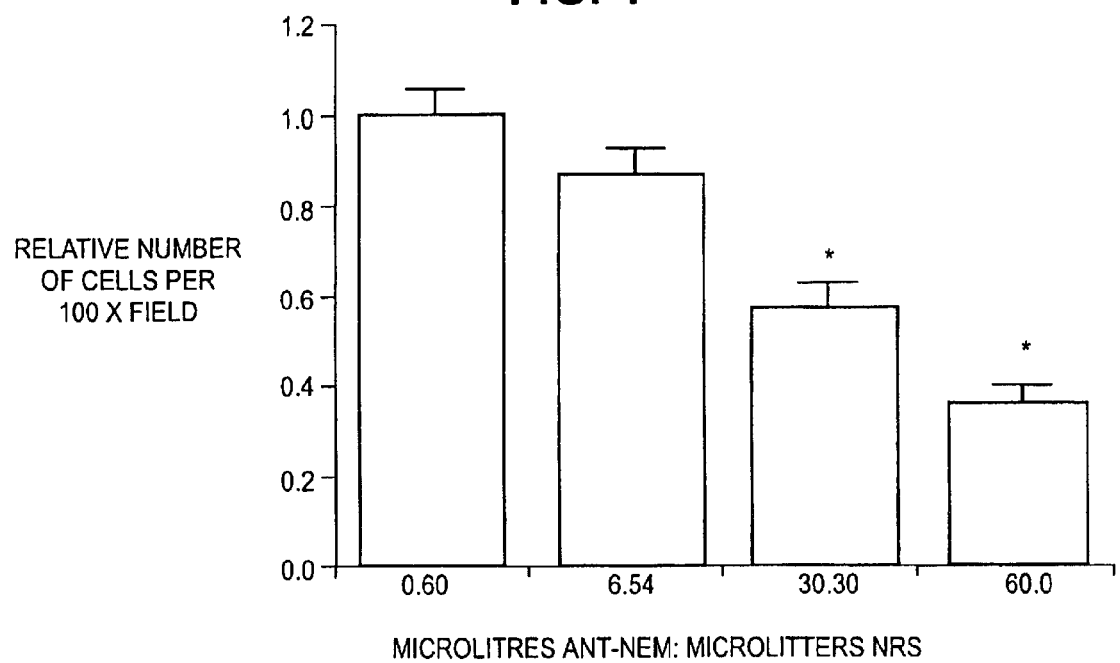
FIG. 4 is a bar graph illustrating a dose-dependent inhibition of invasiveness of PC-3M cells by anti-NEM antiserum.

FIG. 4 illustrates the effect of the anti-NEM antiserum on invasion of PC-3M cells. The invasion assays were performed as described in conjunction with FIG. 3. Instead of stimulating PC-3M cells with NEM, the cells were treated with various concentrations anti-NEM serum. The parallel controls received equivalent amounts of non-immune rabbit serum. The results show that anti-NEM serum significantly reduced invasiveness of PC-3M prostate cancer cells and the decrease was significant at concentrations of 1:50 and 1:100.

7. Detection of Prostatic NEM Peptide in PC Biopsies

FIG. 5 illustrates the detection of the peptide in PC biopsies (BPH-PIN-tumors of various grades). Paraffin-embedded sections were cut at 0.5 mm thickness. Paraffin sections were air-dried for 30 minutes, oven-dried, deparaffinized and rehydrated. Slides were microwaved on "high" with ChemMate antigen retrieval solution (BioTek, Santa Barbara). As a control for nonspecific staining, some of the anti-NEM serum was preabsorbed with 10 μM NEM for one hour at 37° C. prior to use. Non-absorbed and preabsorbed antisera were diluted at 1:70 in Antibody Dilution Buffer (BioTek). Avidin-biotin complex staining was carried out on a Tech Mate 1000 (BioTek) apparatus with ChemMate reagents. All slides were stained with ethyl green for 1 minute, cleared in butyl alcohol, rinsed in xylene and coverslipped. Cytoplasmic and nuclear staining of prostatic epithelium were scored on a scale from 0 (absent) to 4+ (strong and abundant) for a given cell type. Staining was scored as the sum of two components. First, the percent positive cells staining was determined as: <5% neg., 5–25% as 0.5, 35–50% as 1.0, 50–75% as 1.5 and 75–100% as 2.0. The intensity was then determined as: 0.5 for trace, 1.0 for low, 1.5 for moderate, and 2.0 for strong. Diagnosed Gleason grades were reassessed and compared with staining intensity in a paired correlation for n=20 cases. Among n=8 cases with both PIN and prostatic carcinoma, staining of these lesions was compared over the range of Gleason scores using a two-tailed t-test, assuming unequal variances. Also evaluated were staining of lymphocytes, urothelium, seminal vesicles and stroma. Statistical analysis used MS Excel 4.0 spreadsheet software. Significance was based on correlation coefficients with 2 degrees of freedom.

Staining data were also assessed by image analysis on 35 mm Kodak Ektachrome slides of benign, PIN and invasive cancer acini. Slides were scanned by a Polaroid SprintScan 35 scanner at 337 dots/inch and saved as JPEG images using an Adobe Photoshop program. The staining of cytoplasm of 50 cells per image was assessed using an NIH Image program, and the mean staining for each image was calculated. The overall means±standard error were calculated for benign, PIN and invasive carcinoma acini and significance based on 2-tailed t-tests, assuming unequal variances.

Figure 5A:
FIG. 5a is prostate cancer tissue at a premalignant stage (PIN)
Figure 5B:
FIG. 5b is of a moderate grade tumor.
Figure 5C:
FIG. 5c is of an aggressive, high-grade tumor.
Figure 6A:
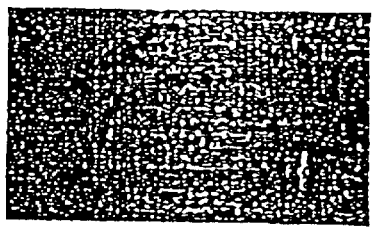
FIG. 6 is a series of photographs of prostate epithelium tissue samples following in-situ hybridization using prostatic mRNA to illustrate the expression of NEM mRNA in: (a) BPH 1; (b) PIN 2; (c) low grade tumor 1; (d) moderate grade tumor 2; (e) high grade tumor 2; and (f) very aggressive tumor 1. The NEM mRNA is expressed only by blue stained cells (primarily basal cells).
Figure 6B:
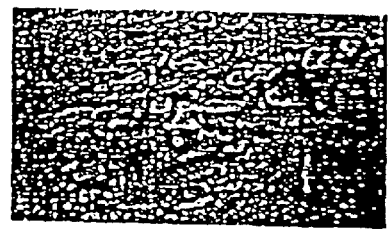
Figure 6C:
Figure 6D:
Figure 6E:
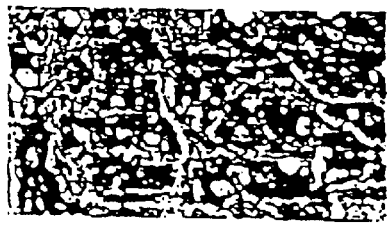
Figure 6F:

A typical NEM staining profile obtained in PC specimens of different grades is presented in the photographs of FIGS. 5a–c. A total of 47 specimens were analyzed, and the results are presented in the following table.

|  | Benign Acini | PIN Acini | Carcinoma |
| --- | --- | --- | --- |
| number of cases analyzed | 19 | 8 | 20 |
| mean ± SEM | 33.51 ± 3.01 | 48.62 ± 3.11* | 65.25 ± 2.81* |

NOTE:
"SEM" means standard error of mean.
"*" means significantly different from benign acini.

FIG. 6 illustrates the detection of the mRNA in PC biopsies (BPH, high grade PIN-tumors of various grades). The data clearly shows that while there is very little or no NEM expression in BPH tissues, it is clearly evident in high-grade PIN (prostatic, intraepithelial neoplasia) considered to be a pre-cancerous state. The data also clearly shows that NEM expression increases proportionally with the grade of cancer (as determined by Gleason score). Thus NEM seems to be a good biochemical marker for prostate cancer and also a good marker for determining the grade of prostate cancer. These experiments demonstrate the use of the immunohistochemical detection of NEM in prostate cancer biopsies and tissues for determining the grade of prostate cancer.

8. Preparation of DNA Probes

Partial complementary DNA (cDNA) for prostatic NEM was cloned into pGEM-T plasmid (Promega, Madison, Wis.) was linearized with Sac II to make antisense strand and with PstI to make sense strand. The transcription reaction and digoxigenin 11-UTP (Boehringer Mannheim, Indianapolis, Ind.) labeling were performed with either SP6 (antisense) or T7 (sense) RNA polymerase provided in the riboprobe labeling kit (Promega). The labeled probes were digested with deoxyribonuclease (Boehringer), extracted with pheno-chloroform, and purified with TE Microselect-D G-50 spin columns (5 Prime-3Prime, Inc., Boulder, Colo.).

9. Detection of PC Using In-Situ Hybridization

Figure 7A:
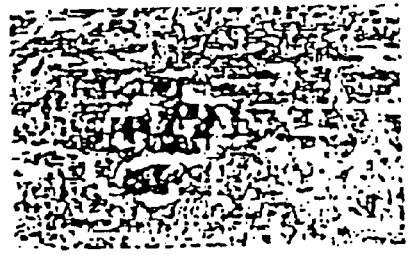
FIG. 7 is a series of photographs of tissue samples following in-situ hybridization using prostatic NEM mRNA illustrating that the metastases are prostatic in origin in the liver (a); lymph node (b); and tonsil (c).
Figure 7B:
Figure 7C:
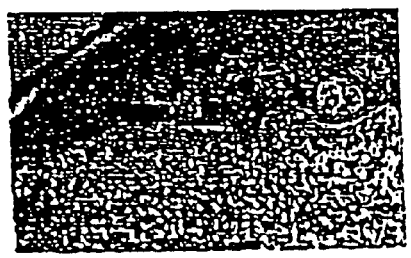

Slides of paraffinized prostate tissue sections were deparaffinized, and the ISH procedure was performed with the antisense mRNA probe as described by Panoskaltsis-Mortari and Bucy. As a negative control for ISH, the sense mRNA strand was substituted. The hybridization was performed overnight at 42° C. The washing of the sections was performed with 0.5%×SSC at 42° C. After the washing, the sections were incubated with mouse anti-digoxigenin antiserum conjugated to alkaline phosphatase. The color development of digoxigenin-coated alkaline phosphatase was carried out using BCIP-NBT substrate system (Bio-Rad) and the sections were counterstained with fast red. The results presented in the FIGS. 6a–f, 13–14 demonstrate the expression of NEM mRNA in prostate epithelium. Probes were also used to determine whether metastases were prostatic in origin in the liver, lymph node and tonsil (FIGS. 7a–c).

10. Detection of NEM mRNA Using RT-PCR

NEM mRNA was detected in prostate cancer specimens as well as cell lines using RT-PCR technique according to published procedures. The primers used in this procedure were: agaacctgtgtgctggcta (forward) and catatactaccccggcta (reverse). The total RNA from the specimens was extracted using a Quiagen RNA extraction kit (Quiagen, Calif.) according to the manufacturer's protocols, reverse transcribed using reverse transcriptase and amplified using the previously described primers pair. The reaction mixture was then separated on 1% agarose gel, and the amplicon of approximate size of 350 bp was detected as predicted according to SEQ ID NO: 6 in prostate cancer specimens and DU-145, MCF-7 and PC-3M cancer cell lines. NEM mRNA was also detected by RT-PCR in certain breast cancer tissues demonstrating that NEM may be a marker for other cancers also, particularly the ones that show a high degree of differentiation into the neuroendocrine-type cells like small lung carcinoma, certain pancreatic cancers, renal cancer, adrenomedullary carcinoma etc.

11. Correlation of NEM Levels with PSA Levels

Figure 8:
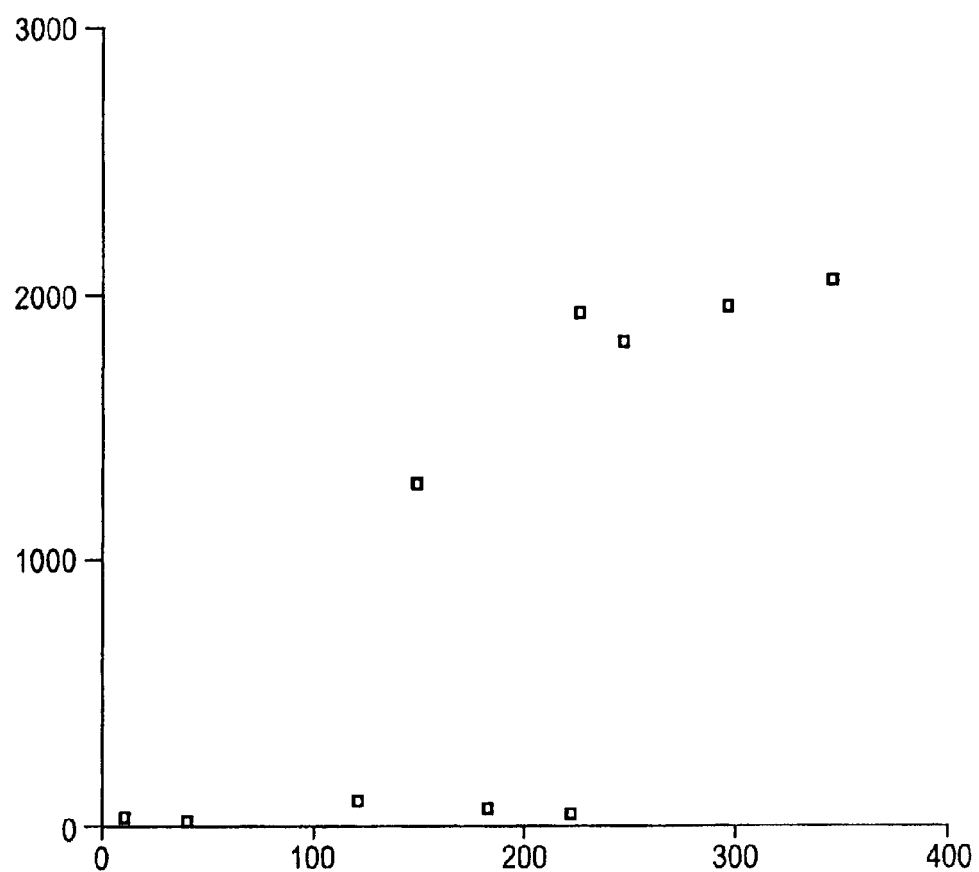
FIG. 8 is a graph illustrating the detection of prostatic NEM in correlation with PSA.
Figure 10B:
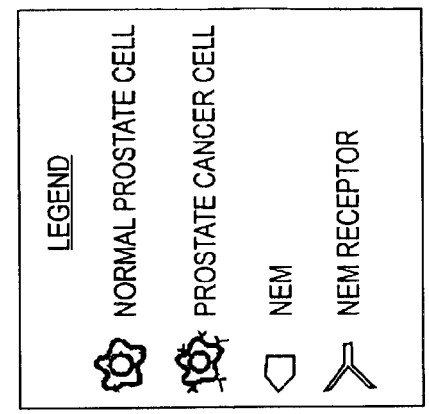
FIG. 10 is a schematic of the mechanism of NEM-mediated proliferation and invasion of prostate cancer cells.
Figure 10B:
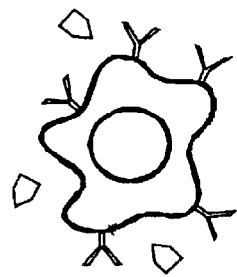
Figure 10D:
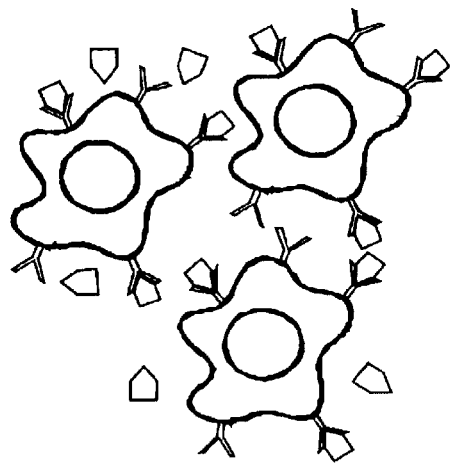
Figure 10A:
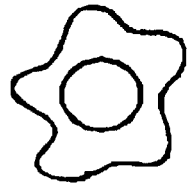
Figure 10C:
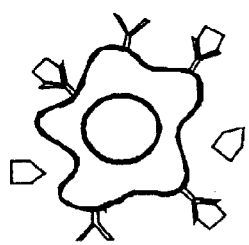
Figure 11C:
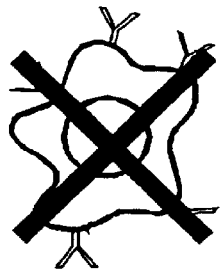
FIG. 11 is a schematic of NEM-based cell-targeted radiation therapy.
Figure 11B:
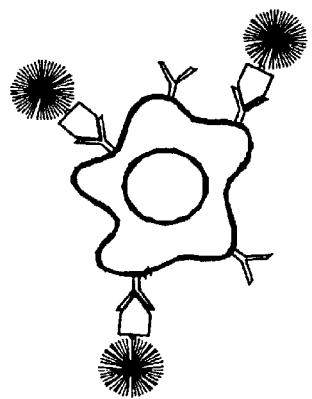
Figure 11A:
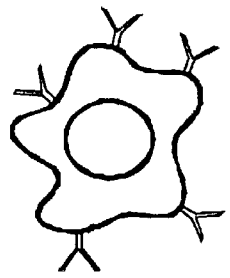
Figure 11D:
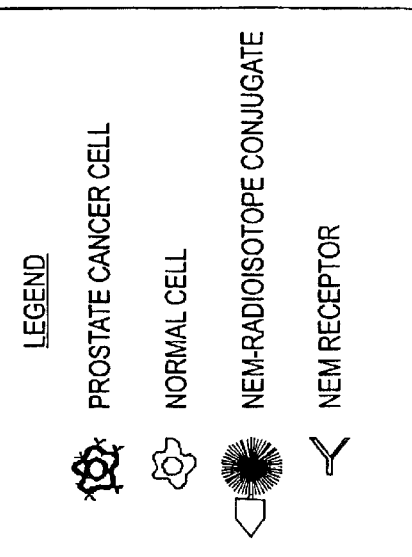
Figure 11D:
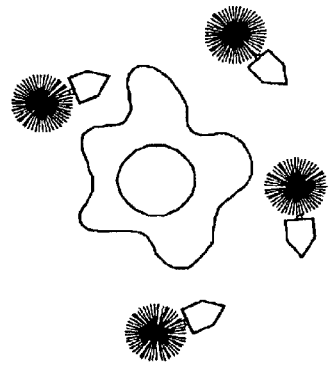

FIG. 8 illustrates the detection of the NEM antigen in serum samples and the correlation with PSA. Serum samples from patients with prostate cancer were obtained from the Department of Pathology and Laboratory Medicine at the University of Kansas Medical Center. Their PSA levels were determined at the Department of Pathology and they ranged from 13.2–2046 units. The samples were then processed for NEM radioimmunoassay (RIA) by standard antigen-antibody reaction. In this procedure, the serum samples were processed (for the removal of macromolecules) by precipitating w/acetate-ethanol and the supernatant was passed through a 0.5 ml Sephadex 625 column. The fractions containing the peptide were used for assays. The processed serum samples are incubated are incubated with anti-NEM serum for 24 hours at 4° C. $I^{125}$-labeled NEM is then added (approximately 30,000 cpm). The samples are then incubated for an additional 24 hours. At the end of incubation, the samples are treated with 4V of chilled ethanol, centrifuged and pellet is counted for radioactivity. The values of NEM are derived by log-logit transformation of the data. The results are plotted as NEM levels (pg/ml) against PSA levels (units).

The results obtained following this procedure suggest a high degree of correlation between PSA levels and NEM levels in 8 of the 10 samples assayed. The degree of correlation was 0.772 and was statistically significant ($p<0.01$). Furthermore, 2 samples that had low PSA levels exhibited significantly higher NEM levels. These preliminary results suggest that NEM may provide an additional paradigm for the detection of PC and other cancers that exhibit increased production of NEM. In addition, it can be useful in detecting PSA-negative PC cases.

12. Preparation of Vectors for RNA Synthesis and Antisense RNA, Ribozymes and Aptamer Synthesis The NEM cDNA can be expressed in laboratory conditions or in vivo when the cDNA of the reported sequence or its antisense sequence or a ribozyme targeted against NEM mRNA or an aptamer sequence that binds NEM is cloned downstream of a promoter in a vector(s) which includes, but is not limited to, a viral vector or a plasmid vector under the control of a promoter where the promoters are chosen from a panel of eukaryotic promoters including, but not limited to, SV40 immediate early promoter, cytomegalovirus promoter, thymidine kinase promoter, Maloney murine leukemia virus long terminal repeat, U1 promoter, U6 promoter, tRNA promoter and VA promoter.

The NEM cDNA or its antisense (when transcribed in the reverse direction), ribozyme or aptamer can be formulated in a carrier for delivery to the prostate cancer cells and can be administered to patients through intravenous, intramuscular, subcutaneous injections or direct injections into the tumor tissue.

13. NEM Vaccine

NEM expression cassette can also be used for immunotherapy. The NEM cDNA vaccine construct, which encodes for NEM can be directly inoculated into the host. The expression cassette will be under the control of a strong promoter such as a cytomegalovirus promoter. The transfected cells then become the production source of the NEM, and can sensitize immune cells against NEM. The sensitized immune cells become capable of destroying NEM producing endogenous prostate cancer cells. A similar approach using pCMV-PSA expression cassette has shown that a strong and persistent antibody response against PSA, a prostate protein, is observable for at least for six months after immunization. Alternate approaches may include injecting NEM after conjugation with other protein or glycoproteins to enhance their immune recognition or injecting these conjugates using lipid formations. Use of the above methods in addition to eliciting cellular immunity could also induce humoral immunity (production of NEM specific antibodies). Such antibodies against NEM produced by the patients receiving NEM vaccine would neutralize the NEM produced and secreted by cancer cells, which would neutralize the growth and invasion-promoting action of NEM thereby providing additional therapeutic benefits.

14. Preparation of Monoclonal, Single Chain, Phage-Display Selected, and In Vitro Evolved Antibodies to Prostatic NEM A. Polyclonal Antibodies The antibody to NEM is produced when the NEM peptide of Sequence Nos. 1–6 or its precursor or fragments are conjugated to a large protein molecule by covalent linkage, mixed with an adjuvant and injected into either a rabbit, mouse or other host to generate an immune response. The serum or the spleen of the injected animal is harvested. The serum was found to contain immunoglobin molecules generated in response to NEM, such molecules being capable of recognizing various antigenic sites on NEM and, thus, are called polyclonal antibodies. The serum is tested for the immune response whereas spleen cells are fused with tumor cells to generate hybridomas. The fused cells that secrete the antibody to NEM are thus immortalized and each cell secretes an immunoglobin molecule that recognizes a single antigenic site of NEM. The antibodies can also be obtained by phage display when the expression vector (described above in "Preparation of Vector for RNA Synthesis") is injected into an animal.

More specifically, the antibody to NEM is generated when purified or synthetic NEM peptide (or its fragment, precursor or other modified form) is conjugated to key hole limpet hemocyanin by covalent linkage, mixed with an adjuvant and injected into either a rabbit, mouse or other host to generate an immune response (according to published procedure in Harlow, et al., Antibodies: A Laboratory Manual (1988) Cold Spring Harbor Laboratory, NY). The serum of the animal is then obtained. The serum contains immunoglobulin molecules generated in response to NEM injections which can recognize various antigenic sites on the NEM sequence. The IgC function of this serum is used for diagnostic purposes such as immunohistochemistry (as demonstrated by FIG. 5), immunoassays (as depicted in FIG. 8), and is also used for the immunoneutralization of NEM (as presented in FIGS. 3 and 4) or passive immunization of animal models.

B. Monoclonal Antibodies

Purified NEM or a synthetic fragment of the peptide is conjugated to an immunogen like keyhole limpet hemocyanin or similar protein according to published procedures (Harlow, et al., supra). The conjugated immunogen is injected into a mouse and monoclonal antibodies are prepared according to published procedures. Several hybridoma clones secreting the murine monoclonal antibodies are isolated and the antibodies secreted by the cells are tested for their ability to bind to radioiodinated NEM. Generally, the hybridoma clones secreting antibodies with the highest affinity are selected. These antibodies are further tested for their ability to inhibit the growth and invasive properties of prostate cancer cells as described above.

The hybridoma culture is then scaled up in large bioreactors as is known in the art to produce large amounts of monoclonal antibodies. The antibody that is secreted into the cell culture media is purified using standard chromatographic methods and is used for diagnostic purpose or administered to prostate cancer patients as an aqueous formulation intravenously.

15. NEM Antibody for the Treatment of Prostate Cancer

Currently, no effective therapies are available for the treatment of advanced prostate cancer. Surgical removal of the lesion, although effective if performed during the early stages of the disease, is not effective when the cancer has spread to distant locations. Accordingly, there is an unmet medical need for new drugs that are more effective than current alternatives.

An ideal therapeutic agent against prostate cancer should minimally possess three qualities: (1) It should interfere with the growth of prostate cancer cells; (2) it should prevent the spread of prostate cancer cells; and (3) it should be minimally toxic to normal cells.

Figure 12:
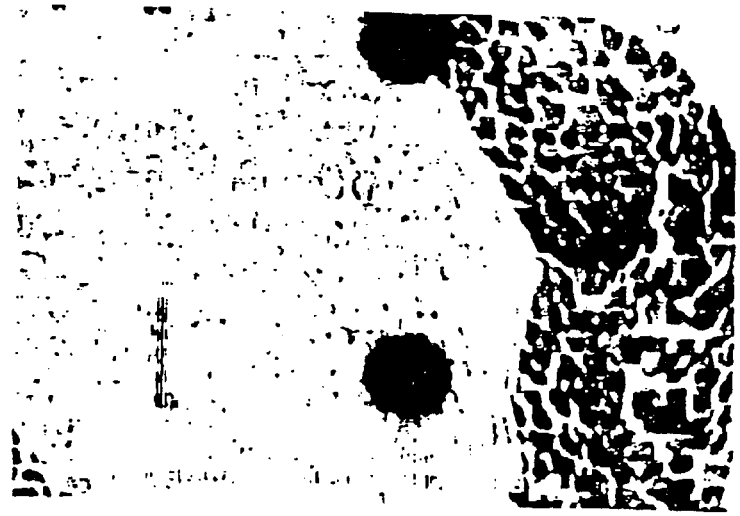
FIG. 12 is a series of photomicrographs depicting NEM selectively binding to prostate cancer cells.
Figure 13A:
FIG. 13 is series of photomicrographs of immunohistochemical detection of NEM in prostate cancer tissue sections, and detection of NEM in secondary sites of prostate cancer.
Figure 13B:
Figure 13C:
Figure 13D:
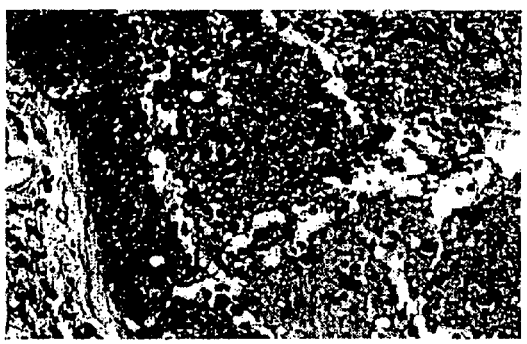
Figure 13E:
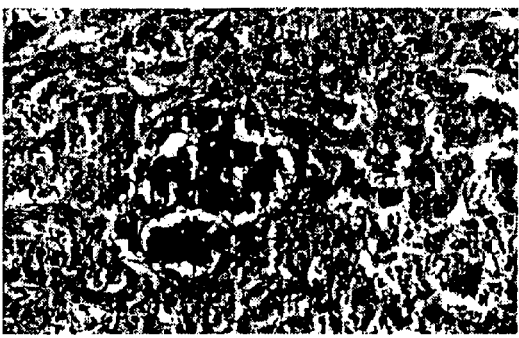
Figure 14A:
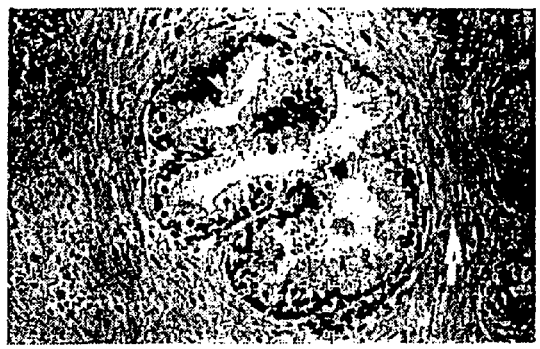
FIG. 14 is a series of photomicrographs of the expression of NEM in BPH and prostate cancer tissue sections.
Figure 14B:
Figure 14C:
Figure 14D:
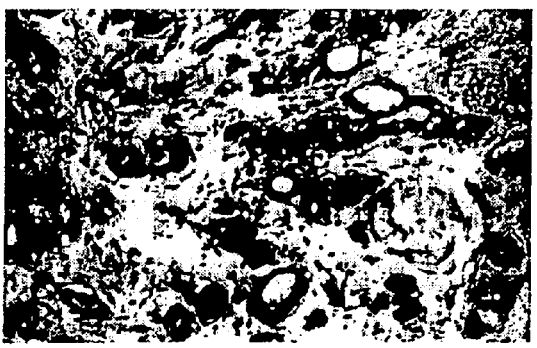
Figure 14E:
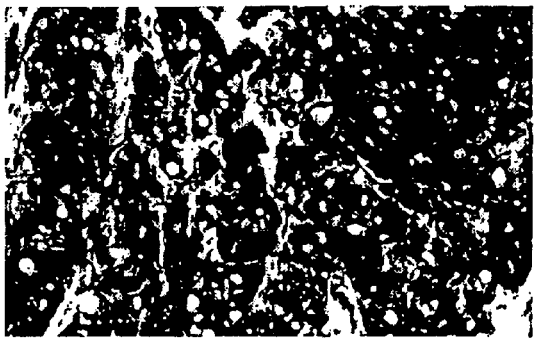
Figure 14F:
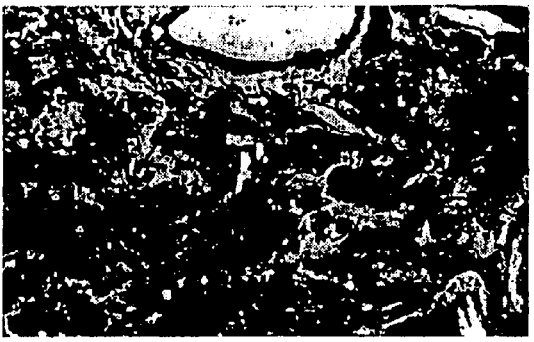

Antibodies directed against NEM block the growth and the metastatic potential of prostate cancer cells grown in culture. As shown in FIG. 12, NEM selectively binds to NEM receptors on prostate cancer cells. The binding of the antibodies to NEM prevents NEM's interaction with its specific receptors, thereby inhibiting its growth promoting and metastatic properties. The pathway is illustrated in FIG. 9.

Based on the results discussed above, use of antibodies directed against NEM could be used as an effective therapy for prostate cancer. These antibodies could be administered alone or in conjunction with one of the currently available therapies. This type of combination therapy is being increasingly used for the treatment of a variety of diseases. Antibodies, particularly humanized monoclonal antibodies, or human antibodies, are gaining acceptance as therapeutics designed to block the action of various bioactive molecules involved in disease processes, and specifically for the treatment of cancer. An example is the use of antibodies against HER2, a receptor protein that is expressed in high amounts in breast cancer and which mediates the action of certain peptide growth factors that induce breast cancer growth. These antibodies have shown efficacy in the treatment of breast cancer in animal models and in humans.

16. Humanized Monoclonal Antibodies Against NEM for the Treatment of Prostate Cancer Repeated administration of murine antibody (similar to the one mentioned above) to humans results in the generation of human anti-mouse antibody and eventual neutralization of the murine antibody. Humanization of the antibody or converting the murine antibody into a predominantly human antibody therefore reduces or prevents the formation of such human anti-mouse antibody. This technique involves cloning the variable regions of the murine antibody, which determines the specificity of the antibody towards an antigen into the constant regions of a human antibody. The variable region that determines the specificity towards an antigen is restricted to a few amino acids and hence the new hybrid antibody would be of predominantly human nature thus preventing the formation of antibodies against it once they are injected into humans. In addition, humanized antibodies have longer retention times in the body thereby allowing fewer doses of the antibody to the patient. Several such "humanized" monoclonal antibodies are in clinical trials for various indications.

EXAMPLE 1

Treatment of Prostate Cancer

In this embodiment, hybridoma-producing monoclonal antibodies against NEM are prepared as above. The cDNA encoding the heavy and light chain of the antibody is isolated from the selected hybridoma using standard recombinant DNA techniques. The VH and VL domains of the murine antibody is fused at the DNA level to the human Ck and Cg domains (CH1, hinge, CH2 and CH3) of the human antibody again using standard recombinant DNA technology. Grafting loops of the VH and VL domains onto human V domain framework can compensate the loss of affinity sometimes observed with this procedure. The chimeric humanized antibody gene is cloned into a mammalian plasmid vector with a drug selection marker (e.g., neomycin selection marker) and the plasmid transfected into a human myeloma cell line. Stable cell lines producing the chimeric humanized antibodies are selected using the drug selection marker. The recombinant antibody is tested for its cross reactivity with NEM and its ability to inhibit the growth and invasion of prostate cancer cells. Selected myeloma cells are scaled up as mentioned above and the purified antibody is used for the treatment of prostate cancer.

EXAMPLE 2

In-Vitro Production of Human Antibodies Against NEM for the Treatment of Prostate Cancer In this embodiment, human B cells are grown in vitro and NEM is added to the cells in presence of certain ligands like CD40 and human T cell clones. Some of the human B cells immunized in vitro can undergo clonal selection and isotype switching. The clones of the B cells producing NEM antibodies with high affinity are selected. The cDNA encoding the antibody is isolated and transfected into human myeloma cells and stable cell lines producing the human antibody against NEM are selected, scaled up and the antibodies purified by methods mentioned above.

EXAMPLE 3
Production of Humanized Antibody in Transgenic Mice

In this embodiment, NEM, or peptides derived from NEM, are injected in its native form or conjugated to immunogen like keyhole limpet hemocyanin and injected into transgenic mice that carry human V-genes. These mice are defective for the expression of their endogenous (mouse) V genes. This results in the production of antibodies against NEM that utilize the human V genes. The murine B cells that secrete human antibodies are then immortalized by fusing to human myeloma cells using known procedures. The immortalized human myeloma cells producing the human antibodies are scaled up, purified from the cell culture medium, and used for the treatment of prostate cancer.

EXAMPLE 4
Detection of Prostatic NEM in PC Biopsies Using Immunofluorescence Prostatic NEM can be detected in PC biopsies by immunofluorescence. The frozen PC specimens are sectioned to 5–10 μm size, fixed in Zamboni's fixative and incubated with NEM antiserum for 24 hours at 4° C. The sections are then washed and incubated with anti-rabbit (or mouse) immunoglobulins linked to fluorophores such as FITC, rhodamine, Texas Red or other dyes. The sections are then washed, mounted and observed under the fluorescence microscope with appropriate filters.

EXAMPLE 5
Preparation of Aptamers, Complex Sugars, Organic Compounds and Inorganic Compounds Capable of Binding to Prostatic NEM An aptamer is either an RNA, DNA or composed of other modified nucleosides that can bind sequences encoded by cDNA Sequence IDs 2, 3, 4, or 5. A complex sugar molecule, an organic compound or an inorganic compound that can also bind to the peptides of NEM, or its fragments, precursor or homologue. A frozen section of human prostate cancer specimen was probed with anti-NEM IgG. The antibody was removed, washed and incubated with anti-rabbit IgG-FITC. The presence of NEM-immunopositive cells along the acinar regions was observed.

Serum prostatic NEM can be detected using many known techniques such as radioimmunoassays, fluorescence immunoassays, ELISA, EIA and the like and as generally described in Rose, et al., Manual of Clinical Laboratory Immunology (1997).

EXAMPLE 6
Radioimmunoassay (RIA)

Radioactive isotopes can be easily incorporated into NEM and can be easily detected. A radioimmunoassay is a competitive immunoassay where a fixed number of antibody sites are made to react with two sets of antigens (i.e., NEM and NEM*R-NEM incorporated with a radioisotope). NEM is usually present in variable amounts either in serum samples (unknown amounts) or in standard solutions (where known amounts of NEM are added in variable amounts in series of dilutions). The radioisotope incorporated into NEM is generally either $I^{125}$, 3H or other molecule. The NEM*R is added in fixed amounts (as assessed by radioactive counts per minute or cpm, NEM+NEM*R+As-NEM=NEM-As-NEM+NEM*R-As-NEM (radioactivity or cpm). Since fixed amounts of anti-NEM molecules are made to react with fixed number of NEM*R molecules and variable numbers of NEM molecules, the resulting concentration of NEM*R-As-NEM conjugate molecules will be inversely proportional to the concentration of NEM.

The method for conducting NEM RIA comprises: (1) preparing NEM samples; (2) incubating the samples with NEM antiserum; (3) adding NEM*R; (4) terminating the reaction and precipitating the NEM*R-As-NEM complexes; and (5) measuring radioactivity and calculation.

1. Preparation of NEM Samples

The unknown serum NEM samples (e.g., patient serum) needs to be partially purified. Since NEM is a small peptide molecule, NEM*R can conjugate with various other protein molecules in serum giving rise to very high non-specific binding. The serum samples are precipitated with ethanol acetate, centrifuged and the supernatant is passed through a Sephadex G25 column. The fraction containing NEM are used for the assay.

2. Incubation

Purified serum samples or standard NEM samples (known amounts of NEM added in the assay buffer) are incubated with anti-NEM serum.

3. Addition

The NEM*R (approximately 25,000 cpm) is added to each tube and the incubation is continued.

4. Precipitation and Measurement

After incubation for 24 hours, the NEM-Antibody-NEM complex is precipitated. The tubes are dried and the pellet is counted for radioactivity. The standard curve is derived by log-logit transformation. The concentrations of NEM in unknown serum samples are calculated from the amount of radioactivity. The sensitivity of the assay is 10–40 pg/tube depending on the stability of NEM*R. As shown in FIG. 8, RIA has been used to measure serum NEM levels in patients with PC.

EXAMPLE 7
Enzyme-Linked Immunosorbent Assay (ELISA)

One or more of the polyclonal antibody, monoclonal antibody, single chain antibody, phage-display antibody, in vitro evolved antibody, and aptamer is conjugated to one or more molecules including, but not limited to, biotin, avidin, fluorescein, rhodamine, alkaline phosphates, horseradish peroxidase and radionuclides such that the conjugate retains its ability to bind prostatic NEM. This conjugate is incubated with serum and the unbound conjugates are removed and the amount of conjugate bound to the NEM is calculated.

EXAMPLE 8
Sandwich ELISA

Sandwich ELISA is an improvement of ELISA that enables one to use unprocessed serum samples for the NEM assay. This eliminates the need for purification of serum samples for the assay and thus improves reliability of the results and simplifies the assay procedure.

Primarily, ELISA plates are coated with the antibody that recognizes one antigenic site of the antigen, which in this case is NEM. Untreated serum samples are added on to wells, and the coated antibody will bind with NEM in the serum samples. Thus, when the samples are washed out with the wash buffer, all other serum components are removed but NEM is retained because of its binding to the coated antibody. Then, a second primary antibody that recognizes another antigenic site of the NEM will react with NEM in proportion to the concentration of NEM. The second antibody is conjugated with a reporter enzyme such as alkaline phosphatase. Therefore, the amount of the antigen can be measured by the color produced on addition of the substrate.

EXAMPLE 9
Fluoroimmunoassay (FIA)

FIA is similar to ELISA but instead of a reporter enzyme, a second antibody is tagged to a fluorophore. Therefore, fluorescence, instead of color reaction, is measured as the end point.

EXAMPLE 10

Chemiluminescence Assay

In the chemiluminescence assay, either NEM or a second antibody is tagged to chemiluminescent compounds such as luciferase or green-fluorescent protein. The light is measured in a luminometer. A standard curve from NEM concentrations is generated and NEM concentrations of unknown samples are derived from this curve.

EXAMPLE 11

Detection of Urine Prostatic NEM

Prostate cancer patients have been shown to release various prostatic products in urine. Since prostatic tumor cells produce NEM, it may also be released into urine. NEM in urine samples can be analyzed using RIA, ELISA, fluoroimmunoassay or chemiluminescence assay as described above. This process could be used to screen for prostate cancer.

EXAMPLE 12

In Vivo Detection of PC in Patients where NEM is Conjugated with a Dye or Radiochemical Since NEM should bind to its receptors present on prostate cancer cells, NEM tagged with a dye or a radiochemical can be injected intravenously into a patient and can be tracked to the prostate by imaging devices. Moreover, the radiochemical-NEM conjugate can selectively bind and destroy cancer cells, and can also be used as noninvasive treatment procedure.

Once the prostate cancer has spread to secondary locations, the only treatment currently available for the patient is androgen ablation therapy. However, the tumor becomes insensitive to this therapy after about 12 to 18 months leaving the patient with hardly any treatment choice. However, if one can detect the location of these secondary tumors, they could be surgically removed if such loci are limited in number. There is an intense search for methods to identify sites of secondary metastasis of various cancers. The most promising approach is the use of a targeting molecule akin to a homing devise that can seek out the tumor. Examples of such molecules are antibodies that specifically bind to a protein that is specific for a particular type of cancer. These molecules are conjugated to a radioisotope like Tc-99. The conjugate once injected into the patient seeks out the tumor as a result of the inherent affinity of the targeting molecule for proteins uniquely present on the cancer cells. The location of concentration of the targeting molecule-radioisotope conjugate (location of the tumor) can be identified with a radioactive scanner such as a gamma scanner. Currently, there are no imaging agents for the detection of prostate cancer and NEM may be suitably positioned to fill this void due. Once the secondary tumor sites are identified, they can be excised thereby allowing another treatment option for prostate cancer patients.

In this example, NEM is conjugated to Technetium 99m (Tc99), although several other isotopes are equally useful for tumor imaging. Several procedures for conjugating radio-isotope to proteins and peptides are published and several use chelation reagents. The conjugate is injected into the cancer patients. After several hours or days scintigraphs are acquired by gamma cameras. Scintigraphy is routinely used with different isotopes for the detection of tumors or other lesions. The scintigraphs reveal the site of accumulation of NEM-Tc99 conjugate, which would indicate the location and extent of primary and secondary prostate cancer.

EXAMPLE 13

D-Peptides Blockers of NEM

NEM binds to its receptors on prostate cancer cells with high affinity (low nM) and initiates biological response. Current pharmacological approaches serve to identify the binding region and biological response regions of a bioactive peptide.

NEM fragments of various sizes are synthesized and used for receptor binding studies as well as for in vitro bioassay such as growth of prostate cancer cells. The smallest fragment that retains the receptor binding ability but fails to generate biological response could serve as a competitive antagonist of NEM. Further modifications in the primary structure of the molecule that would increase stability of the peptide, but would not affect its receptor-binding capacity, would lead to the development of antagonists.

The development of an antagonist could provide a therapeutic approach for the treatment of PC, because when administered, the antagonist will occupy NEM receptors but will not generate biological response. In addition, it will prevent the action of locally produced NEM (by blocking its receptors).

Molecules that can block the ability of NEM to bind to its receptors could prevent the growth inducing and spread of prostate cancer cells. Through the use of "mirror image phage display selection" one can select D-peptides that bind to proteins or peptides (e.g. NEM) with high affinity (T. N. Schumacher et. al., Science, 271:1854 (1996)) and prevent its interaction with its receptor. D-peptides, unlike the natural L-peptides, are not degraded by the peptidases in the body. The technique involves the display of random peptide sequences on a phage filament protein (usually pIII of M13). The phage library is then panned against the target peptide that is chemically synthesized as its D-enantiomer. The phage that binds to the peptide is isolated, amplified in a bacterial host and panned again against the target. After several rounds of selection, the phages that display peptides with high affinity are selected. The sequence of the peptide can be deduced the gene that encodes the filament protein-peptide sequence. An enantiomer of the peptide (mirror image), which is the D form of the peptide, would bind to the L-form of the target peptide.

NEM was synthesized as a D-peptide using conventional peptide synthesis techniques and purified by chromatography. NEM was bound to a plastic petri dish and panned against a phage display library (M13) having 108 individual members. Such libraries are available from commercial sources (e.g., New England Biolabs, MA). The unbound phage was then washed off and the phage bound to NEM was eluted from the petri dish using mild acid. The eluted phage was then grown in an *E.coli* host. The phage was again panned against a fresh petri dish coated with NEM. The cycle of binding and elution was repeated 7–8 times until no more enrichment was achieved. The peptide sequence from several isolated phages was determined by PCR sequencing. The deduced peptide sequences were then synthesized as D-peptides and tested for their ability to block NEM-induced growth and invasion in a prostate cancer cell line. Several candidates were tested for their ability to stop tumor growth and invasion in nude mice implanted with human prostate cancer cells. The active sequence was then tested for its toxicity properties in appropriate animal models and then formulated in an aqueous media and administered to prostate cancer patients in clinical trials.

All variants, homologues, mutated variants, alternatively spliced gene variants, pre-mRNA and mRNA molecules of Sequence IDs 2–5 were identified using known techniques. Promoters driving the expression of Sequence IDs 2–5 were also identified.

Detection of SEQ. ID NO: 3

The expression of the NEM gene can be detected in prostate cancer cells by various techniques such as:

1. Reverse Transcriptase-Polymerase Chain Reaction (RT-PCR) by synthesizing NEM cDNA-specific amplifiers SEQ ID NO: 3 in order to detect the expression of NEM mRNA by RT-PCR.
2. Northern Blot or Slot blot analysis to detect NEM mRNA expression. Total mRNA from the prostate samples is prepared and loaded on to a blot in the slot format or fractionated on denaturing 1% agarose gel and transferred onto nitrocellulose blot, cross-linked and hybridized by a radiolabelled NEM cDNA probe.
3. Preparation of NEM cDNA probe: The probe to detect NEM RNA can be prepared by incorporation of radiochemicals using $P^{32}$ or $S^{35}$ isotopes, by introducing fluorescence or chemiluminescence tags into the cDNA molecule, or by developing antibodies to the incorporated nucleotide. These antibodies are usually conjugated to gold or reporter enzymes such as alkaline phosphatase or horseradish peroxidase.
4. Ribozyme Amplification.

EXAMPLE 14

Treatment of PC Using Gene Therapy

Once the factors and mechanisms that regulate NEM gene expression are identified, the factors that suppress NEM gene expression can be used or administered to inhibit endogenous NEM gene expression. An alternative approach is the targeted synthesis of these modulators in PC cells accomplished by producing recombinant retroviruses such as adenovirus driven by prostate-specific promoters such as PSA and contain cDNAs for NEM gene suppressors in their expression cassette. When injected at the site of tumor, the virus invades the tumor site, enters into cells and incorporates into their genome. Because PSA promoter drives its expression, its expression will be selectively induced in prostate cells and other cells such as blood cells, macrophages or cells of connective tissues. Because of the high efficiency of the viral genome, its expression will be high and will produce large amounts of NEM gene suppressors in the tumor area. These suppressors then act on NEM secretors to attenuate NEM synthesis by tumor cells. This approach could provide a clean, targeted and effective treatment for advanced PC.

EXAMPLE 15

Inactivation of NEM RNA Expression Using Antisense and Ribozyme Sequences

Antisense molecules are gaining importance as tools for specifically inactivating mRNA that code for proteins that are involved in disease processes. Antisense molecules are oligonucleotides that are complementary to a target mRNA. The most commonly used antisense molecules have a DNA backbone, which is stabilized against degradation by endonucleases and exonucleases present in the body by chemical substitution of the phosphate backbone. It is believed that the primary mechanism of antisense action is through endogenous RNase H-mediated cleavage of the RNA at the region of the DNA-RNA hybrid. Improved antisense molecules have a short (7-nucleotide) stretch of DNA flanked by sequences with 2'-substitution. The entire molecule is usually modified in the phosphate backbone to enhance stability. These molecules are more specific and have less toxicity. The backbone substitution of choice is phosphorothioate and the 2' modification includes methyl, ethyl, propyl, methoxyethoxy and allyl.

Since mRNA molecules have very complex tertiary structures, it is impossible to predict which site on a mRNA would be accessible for binding of the antisense molecule. Current methods of determining such accessible sites are random and involve synthesis of a large number of antisense molecules and testing their activity in cells. Once an antisense molecule has been identified that has proper antisense activity and limited toxicity, large amounts of the molecule are synthesized and administered as an intravenous infusion.

Another mode of inactivation of mRNA coding for a protein is through the use of ribozymes, which are molecules that can cleave mRNA. Ribozymes can be designed to cleave specific mRNA by introducing sequences that are complementary to the target mRNA. This would allow the ribozymes to specifically bind to the target mRNA and inactivate it. Ribozymes can be chemically synthesized and administered like a conventional drug or can be expressed in appropriate tissues using viral vectors. In the former case, the molecules are stabilized against nuclease degradation by introducing appropriate chemical substitutions in the molecule.

Triplex molecules bind to the major grove of the DNA usually in the purine rich region and prevent the transcription of the mRNA coding for the protein of interest.

Several 21 nucleotide antisense molecules are synthesized using a standard DNA synthesizer. These molecules are composed of a 7-nucleotide DNA sequence in the middle and two 7 nucleotides 2' O-methyl RNA sequences flanking the central DNA portion. The entire molecule is modified in the phosphate backbone with sulfur substitution (phosphorothioate backbone). Forty sequences complementary to different regions of NEM mRNA are synthesized and purified by reverse phase HPLC method.

The antisense molecules are added to PC-3M cells growing in culture and the ability of the antisense to block growth and invasion and its ability to reduce NEM mRNA are monitored. The more active and least toxic (as measured by cellular toxicity assays) sequences are scaled up and tested in nude mice baring prostate tumor to test the efficacy of the antisense molecule to stop the tumor growth and spread. The best candidate is selected, scaled up and administered as an intravenous infusion in prostate cancer patients to determine the efficacy of these molecules in preventing the growth and spread of prostate cancer.

EXAMPLE 16

Preparation of Prostatic NEM Antagonist-Antineoplastic Conjugates

Compositions to treat prostate cancer are produced using known techniques wherein NEM or NEM antibodies are conjugated to chemotherapeutic agents such as Paclitaxel, Cladribine, Pentostatin, Fludarabine, Carboplain, Isofamide, Octreotide acetate, Mitoxantrone, Streptozocin, Stoposide, Flutamie, Leuprolide, Tamoxifen, Bleomycin, Doxrubicin, Cisplatin, Dacabazine, Daunorubicin, Nitrosoureas, Mithramycin, Cytarabine, Procarbazine, Hydrozyurea, Mitomycin C, Vinca alkaloids, Mitotane, Cyclophosphamide, Progestins, 5-Flurouracil, Actinomycin D, 6-mercaptopurine, and the like. These compositions are made into a pharmaceutically acceptable form for human administration.

EXAMPLE 17

Preparation of Prostatic NEM Antagonist-Radionuclide Conjugates

Compositions to treat prostate cancer are produced using known techniques wherein the above-described NEM immunogens are conjugated to radionuclides such as Ac-225, Ac-227, Au-198, B-11, Bi-212, Bi-213, Br-77, Cf-252, Co-60, Cs-137, Cu-67, Ir-192, Os-194, Pb-203, Pb-212, Pd-103, Pd-109, Ra-223, Ra-226, Re-186, Re-188, Rh-105, Sc-47, Si-28, Sm-145, Sr-89, Sr-90, Ta-182, Tb-149, Th-228, Th-229, W-188, Y-88, Y-90, Y-91, and the like. The compositions are made into a pharmaceutically acceptable form for human administration. As illustrated in FIG. 11, such cell-targeted therapy is employed to selectively kill cancer cells.

EXAMPLE 18

Preparation of Prostatic NEM-Antineoplastic and NEM-Radionuclide Conjugates

This cancer treatment composition is a combination of the above wherein a chemotherapeutic agent and a radionuclide are conjugated to an NEM immunogen and then administered to the patient.

All references cited in this application are hereby incorporated by reference.

While this invention has been described with an emphasis upon preferred embodiments, it will be obvious to those of ordinary skill in the art that variations in the preferred methods of the present invention may be used and that it is intended that the invention may be practiced otherwise than as specifically described herein. Accordingly, this invention includes all modifications and equivalents encompassed with the spirit and scope of the invention as defined by the following claims.

What is claimed is:

1. A composition comprising an isolated polypeptide consisting of an amino acid sequence consisting of SEQ ID NO: 6, wherein the polypeptide is conjugated with at least one binding agent selected from the group consisting of a monoclonal antibody, single chain antibody, and phage-display evolved antibody, and in-vitro evolved antibody.

2. A composition for treating prostate cancer, comprising an isolated polypeptide consisting of an amino acid sequence of SEQ ID NO: 6, conjugated with a binding agent capable of inhibiting binding of the polypeptide to its receptor, thereby inhibiting an ability of the polypeptide to induce prostate cancer cell growth, the binding agent selected from the group consisting of monoclonal antibody, fully humanized monoclonal antibody, polyclonal antibody, antibody selected by phage display selection, single chain antibody, and in-vitro evolved antibody.

3. An isolated polypeptide encoded by the DNA sequence of SEQ ID NO: 3.

4. The composition of claim 1, wherein the at least one binding agent is conjugated with a reporter enzyme.

5. The composition of claim 4, wherein the reporter enzyme is selected from the group consisting of alkaline phosphates and horseradish peroxidase.

6. The composition of claim 1, wherein the at least one binding agent is tagged to a fluorophore.

7. The composition of claim 1, wherein the at least one binding agent is tagged to a chemiluminescent compound or a radionuclide.

8. The composition of claim 7, wherein the chemiluminescent compound comprises luciferase or green-fluorescent protein.

9. The composition of claim 1, wherein the polypeptide is conjugated with at least two binding agents selected from the group consisting of monoclonal antibodies, single chain antibodies, phage-display evolved antibodies, and in-vitro evolved antibodies, the at least two binding agents bound to different epitopes of the peptide such that binding of the first binding agent does not compromise binding of the second binding agent.

10. The composition of claim 9, wherein at least one of the at least two binding agents is conjugated with a reporter enzyme.

11. The composition of claim 10, wherein the reporter enzyme is selected from the group consisting of alkaline phosphates and horseradish peroxidase.

12. The composition of claim 9, wherein at least one of the at least two binding agents is tagged to a fluorophore.

13. The composition of claim 9, wherein at least one of the at least two binding agents is tagged to a chemiluminescent compound or a radionuclide.

14. The composition of claim 13, wherein the chemiluminescent compound comprises luciferase or green-fluorescent protein.

* * * * *